United States Patent [19] — Grunwald

[11] 4,304,453

[45] Dec. 8, 1981

[54] ARTICULABLE ARTICLE CLAMP

[75] Inventor: Davor Grunwald, Winnipeg, Canada

[73] Assignee: Harco Electronics Limited, Winnipeg, Canada

[21] Appl. No.: 119,663

[22] Filed: Feb. 8, 1980

[30] Foreign Application Priority Data

Oct. 26, 1979 [CA] Canada .................................. 338506

[51] Int. Cl.[3] .............................................. H01R 13/62

[52] U.S. Cl. .............................. 339/75 R; 339/253 R; 128/639

[58] Field of Search ................ 339/59 R, 59 L, 59 M, 339/61 R, 61 C, 61 L, 61 M, 74 R, 253 R, 253 F, 253 L, 253 S, 258 R; 128/639, 640, 641, 644, 783, 798, 802, 803; 24/248 R, 248 B

[56] References Cited

U.S. PATENT DOCUMENTS 3,829,826 8/1974 Brown et al. .................... 339/255 R
3,895,635 7/1975 Justus et al. ...................... 339/65 X
4,026,278 5/1977 Ricketts et al. ..................... 128/644

FOREIGN PATENT DOCUMENTS 1241495 8/1960 France ............................ 339/253 R

*Primary Examiner*—Joseph H. McGlynn
*Assistant Examiner*—Frank H. McKenzie, Jr.
*Attorney, Agent, or Firm*—Birch, Stewart, Kolasch & Birch

[57] ABSTRACT

An article clamp particularly useful as an electrode clip and formed of resilient plastic material is provided. The clamp includes an open bottomed box-like enclosure including opposed side walls, frontal and distal end connecting portions as spaced-apart front and rear partial top walls integral with opposed end walls and a pair of supporting flanges extending outwardly form an open bottom. A primary electrical contact plate of a channel-shape and having an access slot therein is disposed across a portion of the open bottom and has an upward extension to enable connection to an electrical lead wire. The clamp also includes an articulable cover which is integral with the box-like enclosure. The cover includes first, second and third swingable members interconnected by means of living hinges. The first and third swingable members are secured to the box-like enclosure by means of living hinges. The first swingable member includes a second cooperating electrical contact plate secured thereto and an operating lever is integrally secured to the third swingable member. In operation, when the primary electrical contact plate is disposed in electrical contact with the stud of a male electrode, the operating lever is urged downwardly to place the second cooperating electrical contact plate into electrical contact with the stud of the male electrode and the third living hinge to a positive over-toggle position to lock the contact plates and the male electrode stud in engagement with one another.

18 Claims, 12 Drawing Figures

72 70 63 58 52 51 61 71 67 19 17 53 60 64 66 55 57 13 56 54

VI
VI

ARTICULABLE ARTICLE CLAMP

BACKGROUND OF THE INVENTION (i) Field of the Invention

This invention relates to an articulable article clamp. More particularly, it relates to such a clamp in the form of an electrode clip for the connection of a lead cable from an electrocardiograph to an electrode which is temporarily secured to a human body.

(ii) Description of the Prior Art

There are many situations where it is desirable to clamp an electrode to an electrically conductive wire. In one specific instance, in order to ascertain electrical phenomena arising from physiological functioning, for example electrocardiographic data associated with the functioning of the heart in patient monitoring uses, it is necessary to apply sensory devices (known as electrodes) to the skin. The electrodes may be applied to the skin by a suction cup, aided by an electrically conductive cream, or they may be glued or taped to the patient's body. The electrode may be provided with a male pin or male snap fastener. Traditionally, the female portion of the snap fastener was intended mechanically to couple to the male portion. Several different types of cable fasteners have been used to couple electrical impulses from the electrode on a patient's body to a cable connected to an electrocardiograph or other monitoring device. In all such electrical connectors in general, and in this case in particular, it is important that a good connection be made by the electrode clip between the electrode and the lead cable.

Many deficiencies exist in such cable fasteners. For example, it was found that in many instances the resulting electrical connection was not noise-free and fatigued easily, causing loose connections. Additionally, since existing cable fasteners were connected by pressing downwardly on the male electrode stud, a hard push was often necessary to make a good connection. The prior types of snap fasteners, though simple and inexpensive to produce, were difficult to repair.

One type of fastener which was developed to attempt to solve this problem was a hairpin and turn-cam fastener. This type of fastener made a good electrical connection when new and allowed simple application. The joint between cable and fastener was by a tubular solderless connector which was crimped on the fastener and the cable, and then covered with shrink tubing. However, this fastener suffered many dificiencies. The fastener was expensive to make. It offered very little strain relief, and physicaly fatigued early in life, thereby causing loose connections. The electrical contact surface consisted of only four pin point surfaces which wore away very quickly. The length of the connector provided leverage which, when lifting the cable, often pried the connector off the snap. Because shielded wire cables work best when the exposed metallic fastenings were as small as possible, the length of this type of fastener was much too great to enhance the benefits of shielded cable.

In an attempt to solve this problem, the cable fastener for electrocardiograph electrodes disclosed in U.S. Pat. No. 3,829,826 issued Aug. 13, 1974 to D. M. Brown et al was provided. In that cable fastener, there was included a metal bracket and a spring wire joined together. The metal bracket had a clearance hole which fit over the male snaps and had an offset to allow connections to cup-mounted snaps. The spring wire provided mechanical retention and, by holding the bracket in contact with the snap, a durable electrical connection. A partial loop on the spring wire formed a finger pad for engaging and disengaging the fastener from the snap. The cable fastener mated with the male snap of an electrocardiograph electrode, for example, as it was mounted on a flat surface or seated in a cup depression. While this cable fastener was successful when new, as the spring became less resilient during use, it became less effective. On the other hand, if the spring were made strong initially, it would be more difficult to use.

In a second solution to this problem, that provided by U.S. Pat. No. 3,895,635 issued July 22, 1975 to G. F. Justus et al, a connector was provided which had a non-conductive body having one end of a cable located therein, carrying an electrical contact plate against which a stud of an electrode was locked by a non-conductive cam lever pivotally mounted on the body portion.

In a third solution, that provided by U.S. Pat. No. 4,026,278 issued May 31, 1977 to J. R. Ricketts et al, the electrode stud was inserted in a keyway hole in a connector secured electrically to the end of a cable, and held in place by a sprung back-up plate.

These latter two solutions, however, suffer the practical deficiency that in securing the connector to the electrode stud some pressure would be applied to the electrode.

SUMMARY OF THE INVENTION (i) Objects of the Invention

Accordingly, it is among the objects of this invention to provide an electrode clip having the following features:

(a) to be easily attached to the electrode terminal male snap without force being transmitted directly downwardly on the electrode;

(b) to be electrically effective and positive to the male snap of the electrode;

(c) not to be detachable without a definite action by the user;

(d) to make positive contact to the electrode male snap through two separate contacts in the clip;

(e) to "lock on" to the electrode so that a user will definitely know when the clip is properly attached;

(f) to connect the metal contacts to a two-conductor wire in such a manner that they do not make contact with one another except through both of them contacting the male snap of the electrode;

(g) to provide a slight interference fit with the top bulbous portion of the male snap;

(h) to make positive but gentle electrical contact with the male snap of the electrode;

(i) to be mechanically robust for substantial continued use and yet to provide adequate strain relief for the attached wire or wires; and (j) to be able to be used in a simple fashion by one hand operation.

(ii) Statement of Invention

Accordingly, by this invention, an articulable clamp is provided which is formed of resilient plastic material, the clamp comprising: (i) a box-like enclosure including opposed side walls, frontal and distal end portions connecting the opposed side walls and an open bottom; (ii) a primary clamping surface having an access slot therein disposed across a portion of the open bottom; and (iii) an articulable cover therefor made of resilient plastic material, the cover including (a) a first swingable member secured to the frontal portion of the box-like enclosure by means of a first living hinge, the first swingable member having secured thereto a second cooperating clamp surface; (b) a second swingable member, secured at one end thereof to the free end of the first swingable member by means of a second living hinge; (c) a third swingable member secured at one end thereof to the free end of the second swingable member by a third living hinge, and to a distal wall of the box-like enclosure by a fourth living hinge; and (d) an operating lever integrally secured to the third swingable member; whereby, when the primary clamping surface is disposed in contact with a surface to be clamped and when the operating lever is urged downwardly toward the primary clamping surface, the first swingable member is urged downwardly to place the second cooperating clamping surface into contact with the member to be clamped, and the third living hinge is moved to a positive over-toggle position to lock the clamping surfaces and the member to be clamped into clamping engagement with one another.

This invention also provides an articulable electrode clamp comprising: (i) a box-like enclosure including opposed side walls, frontal and distal end portions connecting the opposed side walls and an open bottom; (ii) a primary electrical contact plate having an access slot therein, the primary electrical contact plate being disposed across a portion of the open bottom, and including means for connection to an electrical lead; and (iii) an articulable cover therefore, made of a resilient plastic material, the cover including (a) a first swingable member secured to the frontal portion of the box-like enclosure by means of a first living hinge, the first swingable member having secured thereto a second cooperating electrical contact plate; (b) a second swingable member, secured at one end thereof to the free end of the first swingable member by means of a second living hinge; (c) a third swingable member secured at one end thereof to the free end of the second swingable member by a third living hinge, and to a distal wall of the box-like enclosure by a fourth living hinge; and (d) an operating lever integrally secured to the third swingable member; whereby, when the primary electrical contact plate is disposed in electrical contact with an upward stud of an electrode, and the operating lever is urged downwardly toward the primary electrical contact plate, the first swingable member is urged downwardly to place the second cooperating electrical contact plate into electrical contact with the upward electrode stud and the third living hinge is moved to a positive over-toggle position to lock the contact plates and electrode in engagement with one another.

(iii) Other Features of the Invention

By one feature, the frontal and distal end portions constitute spaced-apart fixed terminal cover portions of the box-like enclosure.

By another feature, the box-like enclosure includes a pair of opposed side walls, a frontal wall interconnecting the frontal portions of the side walls and a distal wall interconnecting the distal portions of the side walls.

By a further feature, the clamp includes a pair of supporting flanges extending outwardly from the open bottom.

By a further feature thereof, the frontal and distal end portions constitute spaced-apart fixed terminal cover portions of the box-like enclosure, and the box-like enclosure includes a pair of opposed side walls, a frontal wall interconnecting the frontal portions of the side walls, a distal wall interconnecting the distal portions of the side walls, and further, a pair of supporting flanges extending outwardly from the open bottom.

By another feature thereof, the supporting base flanges are semicircular in plan view.

By still another feature, the primary electrical contact plate comprises a channel-shaped member secured to a portion of the bottom of the box-like enclosure.

By a further feature, the primary electrical contact plate comprises a channel-shaped member secured to a portion of the bottom of the box-like enclosure and the primary electrical contact plate is generally circular in plan view, and is provided with a rearwardly disposed wide entry slit converging to a male electrode-embracing slot, and is provided with an angularly upwardly disposed tab, for providing electrical contact with an electrical lead.

By yet another feature thereof, the distal portions of the opposed side walls cantilever rearwardly and upwardly from the supporting base flanges.

By another feature, the first, second and third swingable members are adapted to be vertically movable between the opposed side walls and the operating lever in its lowermost position is adapted to rest atop the opposed side walls.

By still another feature, the operating lever includes a pair of lateral downwardly depending guiding flanges to cooperate with the opposed side walls.

By another feature, the forward portion of the first swingable member is provided with a lower, forwardly extending flange, adapted to cooperate with an inner face of a rearward cantilevered section of the frontal end wall, in order to limit downward movement of the first swingable member.

By still another feature, the primary electrical contact plate is generally circular in plan view, and is provided with a rearwardly disposed wide entry slit converging to a male electrode-embracing slot, and an angularly upwardly disposed tab, for providing electrical contact with an electrical lead.

By a still further feature, the second cooperating electrical contact plate includes a planar base section and a downwardly angularly depending tab having a male electrode-embracing leading edge.

By other features, these clamps are formed of polypropylene.

BRIEF DESCRIPTION OF THE DRAWINGS

In the accompanying drawings.

Figures 1, 2, 3, 4, 5, 6, 7:
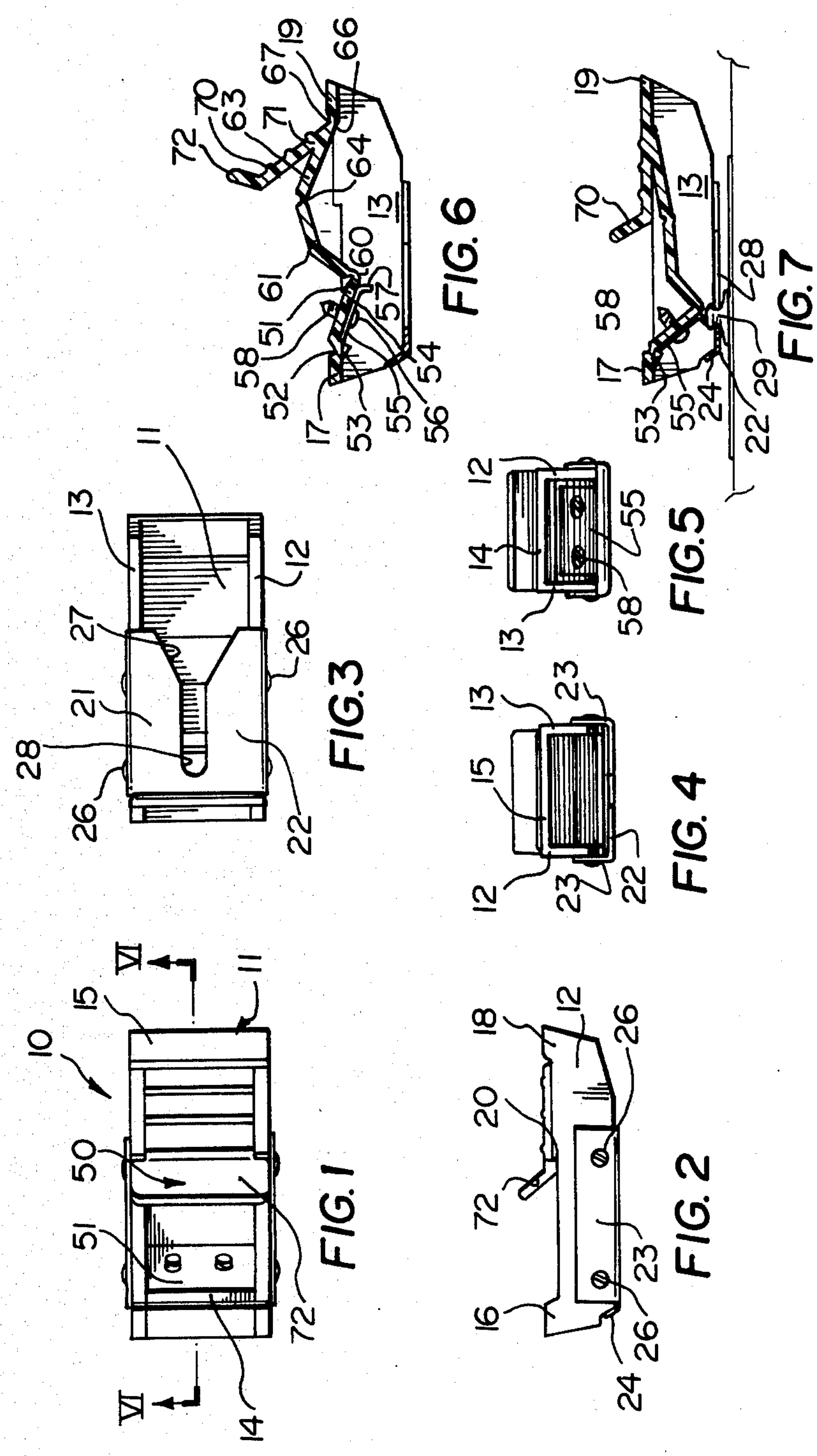
FIG. 1 is a top plan view of the articulable electrode clamp of one embodiment of this invention in its clamped-on association with a male electrode pin.
FIG. 2 is a side elevation of the clamp of FIG. 1.
FIG. 3 is a bottom plan view of the articulable electrical clamp of the embodiment of the invention shown in FIG. 1.
FIG. 4 is a frontal elevational view of the articulable electrical clamp of the embodiment of the invention shown in FIG. 1.
FIG. 5 is a distal elevational view of the articulable electrical clamp of the embodiment of the invention shown in FIG. 1.
FIG. 6 is a cross section through the line VI—VI of FIG. 1, in its open position.
FIG. 7 is a cross section through the line VII—VII of FIG. 1, but in its clamped-on position.
Figure 9:
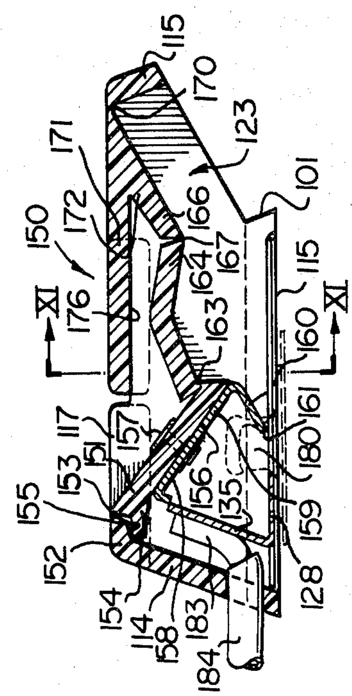
FIG. 9 is a cross section through the line IX—IX of FIG. 8 with electrical contacts shown.
Figure 8:
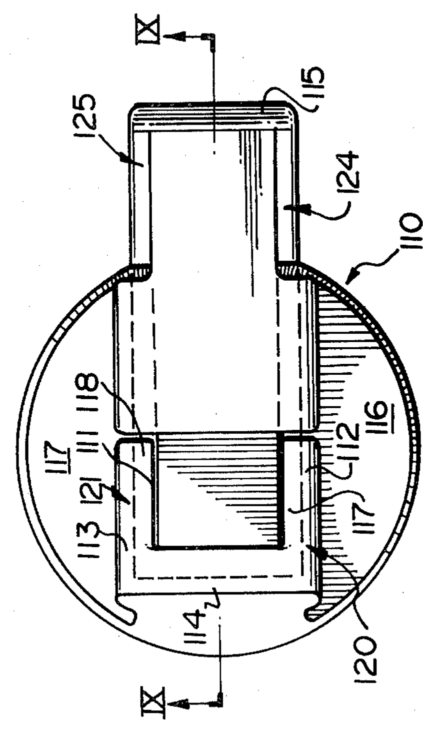
FIG. 8 is a top plan view of the articulable electrode clamp of a second embodiment of the invention, in its closed position.
Figure 11:
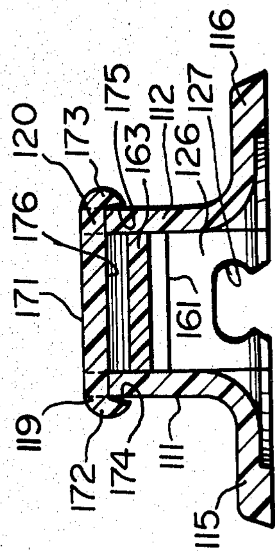
FIG. 11 is a cross section along line XI—XI of FIG. 9.

DESCRIPTION OF PREFERRED EMBODIMENTS (i) Description of FIGS. 1–7

As seen in FIGS. 1–7, one embodiment of the articulable electrode clamp 10 of this invention includes a generally rectangular open bottom box 11, formed of a resilient synthetic plastics material, e.g., polypropylene, and includes opposed side walls 12, 13, frontal end connecting member 14 in the form of a frontal portion of a cover for the box 11, and a distal end connecting member 15 in the form of a distal portion of a cover for the box 11. The frontal portions of walls 12, 13 extend as elevated caps 16, 17 with which frontal connecting member 14 is integrally connected, and the distal portions of walls 12, 13 extend as elevated caps 18, 19 with which distal connecting member 15 is integrally connected. Each side wall 12 and 13 is provided with a shoulder 20, whose purpose will be described hereinafter.

Secured to the open bottom of box 11 is a primary electrical contact plate 21, in the form of a channel member having base 22, upstanding side walls 23 and frontal upward projection 24. Side walls 23 are provided with apertures (not shown) to hold screws 26 which are used to secure plate 21 to box 11. The base 22 of the plate 21 is provided with a converging slit 27 which leads to male electrode snap stub-embracing slot 28. As shown in FIG. 7, the slot 28 embraces snap stub 29.

The articulable electrode clamp 10 is provided with a novel locking cover 50. Cover 50 includes a first swingable member 51 hinged to frontal end connecting member 14 by a first living hinge 52. The underside of the first swingable member 51 below the living hinge 52 is provided with a flange 53 adapted to cooperate with the lower face of frontal end connecting member 14, thereby to limit the downward movement of the first swingable member.

Secured to the inner face 54 of the first swingable member 51 is a second cooperating electrical contact plate 55 composed of a main base section 56 and a rearward depending section 57. Plate 55 is held to swingable member 51 by screws 58 which are also used to secure electrical lead wires (not shown) to the contact plate 55.

Secured to the free end of first swingable member 51 by means of a second living hinge 60 is a second swingable member 61. The free end of second swingable member 61 is secured to one end of a third swingable member 63 by means of a third living hinge 64. Similarly, the free end of third swingable member 63 is secured to the forward edge 66 of distal connecting member 15 by a fourth living hinge 67. First swingable member 51, second swingable member 61, and third swingable member 63 are each narrow enough to be vertically movable between opposed side walls 12, 13.

An operating lever 70 is integrally formed at portion 71 of third swingable member 63, and extends upwardly and forwardly. The major portion of operating lever 70 is narrow enough to fit between opposed side walls 12, 13 but an outwardly upwardly projecting handle portion 72 is wide enough to rest on the upper shoulders 20 of side walls 12, 13, to limit downward movement of the operating lever 70.

(ii) Operation of First Embodiment of the Invention

The operation of the articulable electrode clamp 10 of a first embodiment of this invention is as follows: The articulable electrode clamp 10 is placed in proximity to a male electrode stub 29 so that the slot 28 of primary electrical contact plate 21 is disposed in electrical contact with male electrode stub 29. Lever 70 is then urged downwardly. This causes first swingable member 51 to rotate about living hinge 52 in a clockwise direction, thus urging leading edge 57 of second electrode conract plate 55 into embracing electrical contact with male electrode stud 29. At the same time flange 53 stops against inner face 54.

Also second swingable member 61 is caused to rotate about second living hinge 60 in a counterclockwise direction, while third swingable member 63 rotates about fourth living hinge 67 in a counterclockwise direction. This causes second swingable member 61 and third swingable member 63 to move closer together and to urge third living hinge 64 downwardly to its over-toggle position. Handle 72 of lever 70 is then urged to rest atop shoulders 20 of side walls 12, 13.

The movement of third living hinge 64 to its over-toggle position locks the two electrical contact plates 55 and 21 into locking engagement with male electrode stub 29.

Unlocking is achieved by the simple expedient of raising handle 72 of lever 70 until the third living hinge 64 is no longer in its positive over-toggle position and continuing upward movement to the limit of rotation of living hinge 67.

(iii) Description of FIGS. 8–12

As now seen in FIGS. 8–12, the articulable clamp 110 includes a generally rectangular open-bottomed box 111, formed of resilient synthetic plastics material (e.g., polypropylene) and includes opposed side walls 112 and 113, and opposed frontal wall 114 and distal wall 115. Integral with side wall 112 is an outwardly projecting base in the form of a semi-circular supporting flange 116, and integral with side wall 113 is an outwardly projecting base in the form of a semi-circular supporting flange 117. The frontal portions 118 and 119 of walls 112 and 113 are raised as caps 120 and 121 and are of the same height as frontal wall 114. Similarly, the distal portion (not shown) 123 of walls 112 and 113 cantilever rearwardly and upwardly from base flanges 116 and 117 to terminate in caps 124 and 125 which are of the same height as distal wall 115. Distal wall 115 includes end 126 having a keyhole slot 127 therein.

Figure 12:
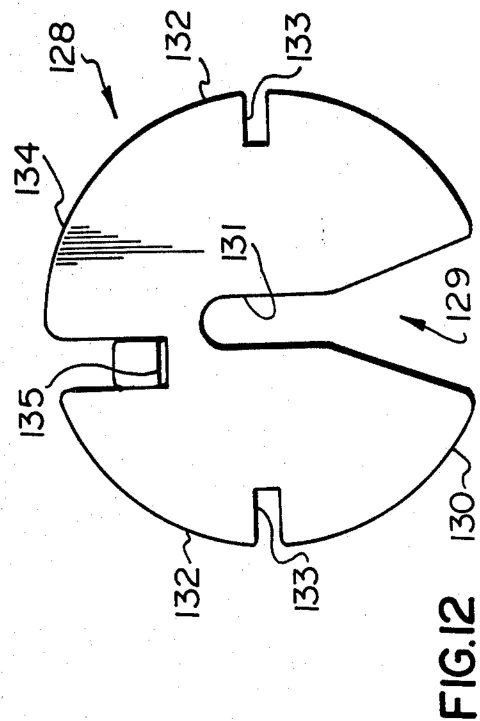
FIG. 12 is a plan view of the primary electrical contact plate of the embodiment of the invention shown in FIG. 8.
Figure 10:
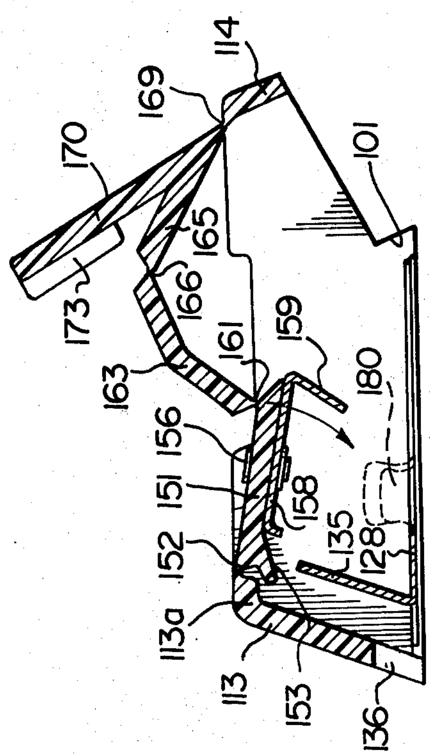
FIG. 10 is a cross section similar to that of FIG. 9 but with the clamp in its open position.

Secured to the open bottom of the box 111 is a primary electrical contact plate 128 which (as seen in FIG. 12) is generally circular in plan view. Plate 128 is provided with a wide slit 129 at its rear circumferential edge 130 which converges to a male electrode stub-embracing slot 131. Diametrically opposed side circumferential edges 132 are provided with mounting slits 133. The forward circumferential edge 134 is provided with an upstanding tab 135 to which is secured the exposed electrical lead wires 136.

The articulable clamp 110 is provided with a novel locking cover 150. Cover 150 includes a first swingable member 151 hinged to a rearwardly cantilevered section 152 of the frontal wall 114 by a first living hinge 153. The forward lower portion of the first swingable member 151 is provided with a lower forward extending flange 154, adapted to cooperate with the inner face 155 of rearward cantilevered section 152 of frontal wall 114, in order to limit downward movement of the first swingable member 151. Secured to the inner face 156 of the first swingable member 151 by means of rivets 157 is a second cooperating electrical contact plate 158, composed of planar base section 159 and downwardly depending tab 160 having a male electrode stub-embracing leading edge 161.

Secured to the free end of first swingable member 151 by means of a second living hinge 163 is a second swingable member 164. The free end of second swingable member 164 is secured to one end of a third swingable member 166 by means of a third living hinge 167. Similarly, the free end of third swingable member 166 is secured to the forward edge of distal wall 115 by a fourth living hinge 170. First swingable member 151, second swingable member 164 and third swingable member 166 are each narrow enough to be vertically movable between opposed side walls 112, 113.

An operating lever 171 is integrally formed at portion 172 of third swingable member 166 and extends in a forward direction. The operating lever 171 is wider than the swingable members 162, 164 and 166 and is provided with downwardly depending flanges 172, 173 (see FIG. 11) to cooperate with the side faces 174, 175 of side walls 112, 113 and to permit the inside face 176 of lever 171 to rest atop side walls 112, 113.

(iv) Operation of the Second Embodiment of the Invention

The operation of the articulable electrode clamp 110 of the second embodiment of this invention is as follows: The articulable electrode clamp 110 is placed in proximity to a male electrode stub 180 so that the slot 131 of primary electrical contact plate 128 is disposed in electrical contact with male electrode stub 180. Lever 171 is then urged downwardly. This causes first swingable member 151 to rotate about living hinge 153 in a clockwise direction, thus urging leading edge 161 of second electrode contact plate 158 into embracing electrical contact with male electrode stub 180. At the same time flange 154 stops against inner face 155.

Also second swingable member 164 is caused to rotate about second living hinge 168 in a clockwise direction, while third swingable member 166 rotates about fourth living hinge 170 in a counterclockwise direction. This causes second swingable member 164 and third swingable member 166 to move closer together and to urge third living hinge 167 downwardly to its over-toggle position. Lever 171 is then urged to rest atop walls 112 and 113.

The movement of third living hinge 167 in its over-toggle position locks the two electrical contact plates 128 and 158 into locking engagement with male electrode stub 180.

Unlocking is achieved by the simple expedient of raising leading edge 181 of lever 171 until the third living hinge 167 is no longer in its positive over-toggle position and continuing the raising motion until the limit of rotation of living hinge 170.

SUMMARY

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. An articulable clamp comprising:

(i) a box-like enclosure including opposed side walls, frontal and distal end portions connecting said opposed side walls and an open bottom;

(ii) a primary clamping surface having an access slot therein disposed across a portion of said open bottom; and (iii) an articulable cover therefor made of resilient plastic material, said cover including (a) a first swingable member secured to said frontal portion of the box-like enclosure by means of a first living hinge, said first swingable member having secured thereto a second cooperating clamping surface;

(b) a second swingable member, secured at one end thereof to the free end of said first swingable member by means of a second living hinge;

(c) a third swingable member secured at one end thereof to the free end of said second swingable member by a third living hinge, and to a distal wall of said box-like enclosure by a fourth living hinge; and (d) an operating lever integrally secured to said third swingable member;

whereby, when said primary clamping surface is disposed in contact with a surface to be clamped and when said operating lever is urged downwardly toward said primary clamping surface, said first swingable member is urged downwardly to place said second cooperating clamping surface into contact with said member to be clamped, and said third living hinge is moved to a positive over-toggle position to lock the clamping surfaces and the member to be clamped into clamping engagement with one another.

2. The articulable clamp of claim 1 wherein said frontal and distal end portions constitute spaced-apart fixed terminal cover portions of said box-like enclosure.

3. The articulable clamp of claim 2 wherein said box-like enclosure includes a pair of opposed side walls, a frontal wall interconnecting the frontal portions of said side walls and a distal wall interconnecting the distal portions of said side walls.

4. The articulable clamp of claim 3 including a pair of cooperating flanges extending outwardly from said open bottom.

5. An articulable electrode clamp comprising:

(i) a box-like enclosure including opposed side walls, frontal and distal end portions connecting said opposed side walls and an open bottom;

(ii) a primary electrical contact plate having an access slot therein, said primary electrical contact plate being disposed across a portion of said open bottom, and including means for connection to an electrical lead; and (iii) an articulable cover therefor, made of a resilient plastic material, said cover including (a) a first swingable member secured to said frontal portion of the box-like enclosure by means of a first living hinge, said first swingable member having secured thereto a second cooperating electrical contact plate;

(b) a second swingable member, secured at one end thereof to the free end of said first swingable member by means of a second living hinge;

(c) a third swingable member secured at one end thereof to the free end of said second swingable member by a third living hinge, and to a distal wall of said box-like enclosure by a fourth living hinge; and (d) an operating lever integrally secured to said third swingable member;

whereby when said primary electrical contact plate is disposed in electrical contact with an upward stud of an electrode, and said operating lever is urged downwardly toward said primary electrical contact plate, said first swingable member is urged downwardly to place said second cooperating electrical contact plate into electrical contact with said upward electrode stud and said third living hinge is moved to a positive overtoggle position to lock said contact plates and electrode in engagement with one another.

6. The articulable electrode clamp of claim 5 wherein said frontal and distal end portions constitute spaced-apart fixed terminal cover portions of said box-like enclosure, and wherein said box-like enclosure includes a pair of opposed side walls, a frontal wall interconnecting the frontal portions of said side walls, a distal wall interconnecting the distal portions of said side walls, and further wherein including a pair of supporting flanges extending outwardly from said open bottom.

7. The articulable electrode clamp of claim 6 wherein said supporting base flanges are semi-circular in plan view.

8. The articulable electrode clamp of claim 5 wherein said primary electrical contact plate comprises a channel-shaped member secured to a portion of the bottom of said box-like enclosure.

9. The articulable electrode clamp of claim 5 wherein said primary electrical contact plate comprises a channel-shaped member secured to a portion of the bottom of said box-like enclosure and wherein said primary electrical contact plate is generally circular in plan view, and is provided with a rearwardly disposed wide entry slit converging to a male electrode-embracing slot, and is provided with an angularly upwardly disposed tab, for providing electrical contact with an electrical lead.

10. The articulable electrode clamp of claim 6 wherein the distal portions of the opposed side walls cantilever rearwardly and upwardly from said supporting base flanges.

11. The articulable electrode clamp of claim 5 wherein said first, second and third swingable members are adapted to be vertically movable between said opposed side walls, and wherein said operating lever in its lowermost position is adapted to rest atop said opposed side walls.

12. The articulable electrode clamp of claim 5 wherein said first, second and third swingable members are adapted to be vertically movable between said opposed side walls, and wherein said operating lever in its lowermost position is adapted to rest atop said opposed side walls and wherein said operating lever includes a pair of lateral downwardly depending guiding flanges to cooperate with said opposed side walls.

13. The articulable electrode clamp of claim 5 wherein the forward portion of said first swingable member is provided with a lower, forwardly extending flange, adapted to cooperate with an inner face of a rearward cantilevered section of said frontal end wall, in order to limit downward movement of said first swingable member.

14. The articulable electrode clamp of claim 5 wherein said second cooperating electrode contact plate includes a planar base section and a downwardly angularly depending tab having a male electrode embracing leading edge.

15. The articulable clamp of claim 1 formed of polypropylene.

16. The articulable clamp of claim 1 wherein said first, second and third swingable members are adapted to be vertically moveable between said opposed side walls and said opposed side walls each include a shoulder whereby the downward movement of said operating lever is limited.

17. The articulable clamp of claim 1 wherein the forward portion of said first swingable member is provided with a lower, forwardly extending flange, adapted to cooperate with said frontal end portion in order to limit the downward movement of said first swingable member.

18. The articulable clamp of claim 1 wherein said second clamping surface includes a planar base section and a downwardly depending tab having a male electrode embracing leading edge.

* * * * *